(12) United States Patent
Sutton et al.

(10) Patent No.: US 9,102,803 B2
(45) Date of Patent: Aug. 11, 2015

(54) PROCESS FOR COATING AN ACTIVE INGREDIENT WITH A UREA-FORMALDEHYDE POLYMER

(75) Inventors: Allen R. Sutton, Corydon, KY (US); Willis Thornsberry, Sturgis, KY (US)

(73) Assignee: Koch Agronomic Services, LLC, Wichita, KS (US)

( * ) Notice: Subject to any disclaimer, the term of this patent is extended or adjusted under 35 U.S.C. 154(b) by 48 days.

(21) Appl. No.: 13/399,231

(22) Filed: Feb. 17, 2012

(65) Prior Publication Data

US 2012/0156275 A1 Jun. 21, 2012

Related U.S. Application Data

(62) Division of application No. 12/282,739, filed as application No. PCT/US2007/063067 on Mar. 1, 2007, now abandoned.

(60) Provisional application No. 60/787,839, filed on Mar. 31, 2006.

(51) Int. Cl.
| | |
|---|---|
| *C05C 9/02* | (2006.01) |
| *C08J 7/06* | (2006.01) |
| *C05G 3/08* | (2006.01) |
| *A01N 25/26* | (2006.01) |
| *C08G 12/12* | (2006.01) |
| *C08G 12/40* | (2006.01) |

(52) U.S. Cl.
CPC ............... *C08J 7/065* (2013.01); *A01N 25/26* (2013.01); *C05C 9/02* (2013.01); *C05G 3/08* (2013.01); *C08G 12/12* (2013.01); *C08G 12/40* (2013.01); *C08J 2361/24* (2013.01)

(58) Field of Classification Search
CPC .................................... C05C 9/00; C05C 9/02
See application file for complete search history.

(56) References Cited

U.S. PATENT DOCUMENTS

| | | | |
|---|---|---|---|
| 3,231,363 A | 1/1966 | Renner | |
| 3,516,941 A | 6/1970 | Matson | |
| 4,013,594 A | 3/1977 | Froehlich et al. | |
| 4,015,970 A * | 4/1977 | Hennart | 71/11 |
| 4,025,329 A * | 5/1977 | Goertz | 504/101 |
| 4,115,100 A | 9/1978 | Schurter et al. | |
| 4,378,435 A | 3/1983 | Takagi et al. | |
| 4,610,715 A | 9/1986 | Monaldi et al. | |
| 4,746,349 A | 5/1988 | Becker | |
| 5,005,771 A | 4/1991 | Pieh et al. | |
| 5,188,654 A | 2/1993 | Manalastas et al. | |
| 5,332,584 A | 7/1994 | Scher et al. | |
| 5,364,438 A * | 11/1994 | Weston et al. | 71/29 |
| 6,936,078 B2 | 8/2005 | Bischof et al. | |
| 2005/0187123 A1 | 8/2005 | Li et al. | |
| 2007/0157689 A1 | 7/2007 | Sutton et al. | |
| 2007/0295047 A1 | 12/2007 | Sutton | |
| 2009/0035384 A1 | 2/2009 | Lambeth et al. | |
| 2010/0206029 A1 | 8/2010 | Sutton et al. | |

FOREIGN PATENT DOCUMENTS

| | | |
|---|---|---|
| EP | 0135714 A2 | 4/1985 |
| WO | 01/79349 A1 | 10/2001 |
| WO | WO 2007087180 A2 * | 8/2007 |

OTHER PUBLICATIONS

Pergopak M 2, 2 pages (evidence).*

* cited by examiner

*Primary Examiner* — Kyle Purdy

(57) ABSTRACT

The present invention relates to novel urea-formaldehyde polymers coated with an active ingredient, a method of making the same, and their use.

21 Claims, No Drawings

PROCESS FOR COATING AN ACTIVE INGREDIENT WITH A UREA-FORMALDEHYDE POLYMER

FIELD OF THE INVENTION

The present invention relates to urea-formaldehyde polymers. More particularly the present invention relates to novel urea-formaldehyde polymers coated with an active ingredient, a method of making same, and their use.

BACKGROUND OF THE INVENTION

The industrial applicability of urea-formaldehyde polymers has been known from some time. These polymers find use in diverse applications from use in the agricultural industry to use as an additive in paper, paint, and varnish applications. In the paper industry, it is known that urea-formaldehyde polymers can be used to improve opacity and printability. However, in agricultural applications, the urea-formaldehyde polymers serve mainly as a carrier for an active ingredient. Typically, the active ingredient is deposited into the cavities and onto the surface of the urea-formaldehyde polymer by dissolving the active ingredient in a solvent, and spraying this solution onto the surface of the urea-formaldehyde polymer in a fluidized bed drier. The solvent is volatized by the hot air in the fluidized bed dryer, producing a urea-formaldehyde polymer coated with the active ingredient.

However, the inventors hereof have discovered that some solvents presently used do not completely volatize, and the incomplete volatilization of the solvent limits the amount of active ingredient deposited onto the urea-formaldehyde polymer carrier. In addition, fluidized bed driers are specialized pieces of equipment requiring extensive and expensive air handling and conditioning capabilities. Therefore, there is a need in the art for a process whereby urea-formaldehyde polymer can be effectively coated with active ingredients.

SUMMARY OF THE INVENTION

The present invention relates to a process for depositing one or more, in some embodiments only one, active ingredients onto urea-formaldehyde polymers comprising contacting, in a drying device, a urea-formaldehyde polymer with a solution comprising a solvent selected from ethers, alcohols, hydrocarbons, halogenated hydrocarbons and aromatic hydrocarbons and an active ingredient under conditions including elevated temperatures and sub-atmospheric pressures.

In another embodiment, the present invention relates to a process comprising adding to a drying device a urea-formaldehyde polymer, a solution comprising a solvent selected from ethers, alcohols, hydrocarbons, halogenated hydrocarbons and aromatic hydrocarbons, and an active ingredient under temperatures effective at volatizing at least a portion of the solvent thus producing an active-ingredient-coated urea-formaldehyde polymer.

In another embodiment, the present invention relates to a urea-formaldehyde polymer having deposited thereon greater than 35 wt. %, based on the weight of the urea-formaldehyde polymer, of an active ingredient.

DETAILED DESCRIPTION OF THE INVENTION

In one embodiment, the present invention relates to a process for depositing active ingredients onto urea-formaldehyde polymers. "Active ingredient" as used herein is meant to refer to compounds, chemicals, etc., that find use in agricultural applications and are commonly applied to urea-formaldehyde polymers. Non-limiting examples of active ingredients suitable for use herein include urease inhibitors, fungicides and insecticides. Urease inhibitor, as used herein, is meant to refer to compounds that interfere with urease activity and reduce urea hydrolysis in soils. In preferred embodiments the active ingredient is a urease inhibitor, more preferably N-n-butyl thiophosphoric triamide ("NBPT").

Urea-formaldehyde polymers suitable for use herein can be selected from any urea-formaldehyde polymers known, and these polymers can be made by any method known in the art. For example, the urea-formaldehyde polymers used herein can be made by the process taught in U.S. Pat. No. 6,936,078, which is incorporated in its entirety herein by reference. Non-limiting examples of urea-formaldehyde polymers suitable for use in the practice of the present include those sold under the name PERGOPAK® by the Albemarle Corporation. In preferred embodiments of the present invention, the urea-formaldehyde polymer is selected from those having a water content of between from about 1 and 80 wt. %, based on the weight of the urea-formaldehyde polymer. In more preferred embodiments, the urea-formaldehyde polymer is selected from those having a water content of between from about 10 and 35 wt. %, based on the weight of the urea-formaldehyde polymer. In a most preferred embodiment, the urea-formaldehyde polymer is selected from those having a water content of between from about 10 and 20 wt. %, based on the weight of the urea-formaldehyde polymer. Exemplary urea-formaldehyde polymers suitable for use herein are those sold under the name PERGOPAK® by the Albemarle Corporation, preferably the PERGOPAK® M line of urea-formaldehyde polymers.

The means by which the one or more active ingredients are deposited onto the urea-formaldehyde polymer is not critical to the instant invention and can be selected from any method known. Preferably the one or more active ingredients are deposited onto the urea-formaldehyde polymer by using a drying device such as a high shear mixer, ribbon drier, blade drier, or other similar device. Preferably the drying device is a ribbon drier or blade drier.

Typically, the one or more active ingredients are deposited onto the urea-formaldehyde polymer by introducing into the drying device a urea-formaldehyde polymer and a solution comprising a solvent and one or more active ingredients, in some embodiments only one, as described above. Solvents suitable for use herein can be selected from any volatile organic solvent that can be solubilize the selected active ingredient. Non-limiting examples of suitable solvents include ethers, alcohols, hydrocarbons, halogenated hydrocarbons and aromatic hydrocarbons. In preferred embodiments, the solvent is selected from ethers, alcohols and hydrocarbons. In more preferred embodiments, the solvent is tetrahydrofuran ("THF"). The inventors hereof have unexpectedly discovered that the use of these solvents allows the practitioner to produce an active-ingredient-containing urea-formaldehyde polymer that has an active ingredient concentration higher than previously achievable. While not wishing to be bound by theory, the inventors hereof believe this higher active ingredient concentration is directly attributable to the solvent selected for two important reasons. Firstly, urea-formaldehyde polymers are typically cross-linked polymers that do not readily solubilize in typical solvents. However, some solvents currently used, most commonly N-methyl-2-pyrrolidinone ("NMP"), in coating urea-formaldehyde polymers are strong enough to swell or partially dissolve the urea-formaldehyde polymers, thus limiting the ability to deposit the active ingredient onto the urea-formaldehyde polymer. Secondly, some solvents currently used do not completely volatize in the processes used to deposit the active ingredient onto the urea-formaldehyde polymers. The incomplete volatilization of the solvent leads to a portion of the urea-formaldehyde polymer being coated with solvent, again limiting the surface area onto which the active ingredient can be deposited.

The solution comprising the one or more active ingredients typically contains from about 50 to about 80 wt. %, based on the weight of the solution, of the one or more active ingredient(s). In preferred embodiment, the solution comprises from about 60 to 70 wt. %, based on the weight of the solution, of the one or more active ingredient(s). In a particularly preferred embodiment, the solution comprises from about 62 to about 68 wt. %, based on the weight of the solution, of the one or more active ingredient(s).

In the practice of this embodiment of the present invention, the urea-formaldehyde polymer and solution can be introduced into the drying device simultaneously, in stages, either the polymer or solution introduced before the other, or any combinations thereof. Thus, this embodiment of the present invention can be either a batch or continuous process. In preferred embodiments, the solution is introduced into the drying device after the urea-formaldehyde polymer. In this and other embodiments, the introduction of the solution is controlled to avoid over-wetting of the urea-formaldehyde polymer. The inventors hereof have discovered that over-wetting can be prevented by introducing the solution into the drying device at a rate substantially equal to the rate at which the solvent volatilizes. The volatilization of the solvent is achieved by operating the drying device under conditions that include elevated temperatures; preferably the drying device is operated under elevated temperatures and sub-atmospheric pressures. Elevated temperatures, as used herein, is meant to refer to temperatures effective at volatilizing at least a portion, preferably substantially all, of the selected solvent, i.e. temperatures above the boiling point of the selected solvent. Preferably the temperatures under which the drying device is operated are in the range of from about 20° C. to about 200° C., more preferably in the range of from about 20° C. to about 100° C., most preferably from about 20° C. to about 50° C. Also, as stated above, it is preferred that the drying device be operated under sub-atmospheric pressures, i.e. under a vacuum. These pressures are preferably in the range of from about 760 mmHg to about 0.1 mmHg, more preferably in the range of from about 500 mmHg to about 50 mmHg, most preferably from about 100 mmHg to about 50 mmHg.

Through the use of the presently disclosed coating process, active-ingredient-coated urea-formaldehyde polymers that are characterized as having an active ingredient concentration superior to those currently available can be produced. Typically the active-ingredient-coated urea-formaldehyde polymers according to the present invention have an active ingredient concentration greater than about 35 wt. %, based on the weight of the active-ingredient-coated urea-formaldehyde polymer. Preferably the active ingredient concentration is in the range of from about 40 wt. % to about 80 wt. %, on the same basis. More preferably the active ingredient concentration is in the range of from about 50 wt. % to about 70 wt. %, on the same basis.

The inventors hereof have also discovered that active-ingredient-coated urea-formaldehyde polymers produced by the present invention have a storage life superior to those made using other solvents such as NMP, thus making the active-ingredient-coated urea-formaldehyde polymers more suitable for use in agricultural applications wherein the function of a urease inhibitor is desired. The storage life of the active-ingredient-coated urea-formaldehyde polymers refers to the loss of active ingredient over time, and is thus an important quality. Longer storage life indicates that the active-ingredient-coated urea-formaldehyde polymers retain the active ingredient for a longer period of time under normal storage conditions. In preferred embodiments, the storage life of the present active-ingredient-coated urea-formaldehyde polymers is at least twice that of active-ingredient-coated urea-formaldehyde polymers that were coated using NMP as a solvent.

The above description is directed to several embodiments of the present invention. Those skilled in the art will recognize that other embodiments, which are equally effective, could be devised for carrying out the spirit of this invention. The following examples will illustrate the present invention, but are not meant to be limiting in any manner.

EXAMPLES

Example 1

Pergopak® M Loading Using a 45.7 wt. % Solution of NBPT (N-n-butylthiophosphoric triamide) in NMP (n-methylpyrrolidinone)

Inside a fume hood 35.1 grams of Pergopak® M, a urea formaldehyde polymer commercially available from the Albemarle® Corporation, was weighed into a stainless steel mixing bowl. Into a 250 ml addition funnel was weighed 88.0 grams of the 45.7 wt. % solution of NBPT in NMP. A section of Tygon® tubing and a plastic pipette were added to the additional funnel to allow for the drop wise addition of the NBPT solution onto the Pergopak® M. The mixer was turn on to speed setting #1. The NBPT solution was added to the solid Pergopak® M over a 10-minute period. After the addition was complete the weight of the contents of the mixing bowl was determined to be 117.3 grams. Another 6.0 grams of the NBPT in NMP solution was added over a 10-minute period via the addition funnel. The mixture was stirred for an additional 20 minutes at mixer speed setting #2. The final weight of Pergopak® M loaded with the NBPT solution was 124.3 grams of an off white compactable solid.

Example 2

Pergopak® M Loading Using a 45.7 wt. % Solution of NBPT (N-n-butylthiophosphoric triamide) in NMP (n-methylpyrrolidinone)

Inside a fume hood 35.4 grams of Pergopak® M was weighed into a stainless steel mixing bowl. Into a 250 ml beaker was weighed 70.6 grams of the 45.7 wt. % solution of NBPT in NMP. The mixer was turn on to speed setting #1. The NBPT solution was added to the solid Pergopak® M using a plastic pipette over a 37-minute period. When approximately half of the NBPT solution was added the mixer speed was increased to setting #2. The mixture was stirred for an additional 10 minutes at mixer speed setting #7. The final weight of Pergopak® M loaded with the NBPT solution was 105.0 grams of an off white compactable solid.

Example 3

Pergopak® M Loading Using a 45.7 wt. % Solution of NBPT (N-n-butylthiophosphoric triamide) in NMP (n-methylpyrrolidinone)

Inside a fume hood 35.6 grams of Pergopak® M was weighed into a stainless steel mixing bowl. Into a 250 ml beaker was weighed 97.7 grams of the 45.7 wt. % solution of NBPT in NMP. The mixer was turn on to speed setting #1. The NBPT solution was added to the solid Pergopak® M using a plastic pipette over a 40-minute period. When approximately 30% of the NBPT solution had been added the mixer speed was increased to setting #2. When approximately 80% of the NBPT solution had been added the solid in the mixing bowl took on a wet appearance and the mixer speed was increased to setting #3. After all of the NBPT solution had been added the mixture was stirred for an additional 11 minutes at mixer speed setting #7. The final weight of Pergopak® M loaded with the NBPT solution was 132.0 grams of an off white compactable solid with a wetted appearance.

Example 4

Pergopak® M Loading Using a 45.8 wt. % Solution of NBPT (N-n-butylthiophosphoric triamide) in THF (tetrahydrofuran)

Inside a fume hood 35.7 grams of Pergopak® M was weighed into a stainless steel mixing bowl. Into a 250 ml addition funnel was weighed 157.5 grams of the 45.8 wt. % solution of NBPT in THF. A section of Tygon® tubing was added to the additional funnel to allow for the drop wise addition of the NBPT solution onto the Pergopak® M. The mixer was turn on to speed setting #1. The NBPT solution was added to the solid Pergopak® M over a 46-minute period. The bowl was rotated by hand during the addition of the NBPT solution to facilitate mixing. The mixture was stirred for an additional 49 minutes and during the last 10 minutes of mixing the mixer speed was increased to setting #6 to break up lumps. The final weight of Pergopak® M loaded with the NBPT solution was 107 grams of a fine white free flowing powder.

Example 5

Pergopak® M Loading Using a 45.8 wt. % solution of NBPT (N-n-butylthiophosphoric triamide) in THF (tetrahydrofuran)

Inside a fume hood 25.7 grams of Pergopak® M was weighed into a stainless steel mixing bowl. Into a 250 ml addition funnel was weighed 126.2 grams of the 45.8 wt. % solution of NBPT in THF. A section of Tygon® tubing was added to the additional funnel to allow for the drop wise addition of the NBPT solution onto the Pergopak® M. The mixer was turn on to speed setting #1. The NBPT solution was added to the solid Pergopak® M over a 42-minute period. The mixer speed was increased to setting #2 after 27 minutes to help break up small aggregates. The bowl was rotated by mechanically using an electric motor during the addition of the NBPT solution to facilitate mixing. The mixture was stirred for an additional 8 minutes at a mixer speed setting #6 to break up lumps. The final weight of Pergopak® M loaded with the NBPT solution was 83.3 grams of a fine white free flowing powder.

Example 6

Pergopak® M Loading Using a 45.8 wt. % Solution of NBPT (N-n-butylthiophosphoric triamide) in THF (tetrahydrofuran)

Inside a fume hood 30.3 grams of Pergopak® M was weighed into a stainless steel mixing bowl. Into a 250 ml addition funnel was weighed 163.3 grams of the 45.8 wt. % solution of NBPT in THF. A section of Tygon® tubing was added to the additional funnel to allow for the drop wise addition of the NBPT solution onto the Pergopak® M. The mixer was turn on to speed setting #1. The NBPT solution was added to the solid Pergopak® M over a 39-minute period. The bowl was rotated by mechanically using an electric motor during the addition of the NBPT solution to facilitate mixing. The mixture was stirred for an additional 25 minutes at a mixer speed setting #2 to break up lumps. The final weight of the Pergopak® M loaded with the NBPT solution was 107.3 grams of a fine white free flowing powder.

Example 7

Pergopak® M Loading Using a 45.8 wt. % Solution of NBPT (N-n-butylthiophosphoric triamide) in THF (tetrahydrofuran)

Into a 1 liter round bottom flask containing 4 internal baffles was weighed 20.6 grams of Pergopak® M. Into a 100 ml graduated cylinder was weighed 77.5 grams of the 45.8 wt. % solution of NBPT in THF and 25.0 grams of pure THF. The flask was attached to a solvent evaporator (Buchi Rotavapor®) and evacuated to a pressure of 26 inch of vacuum. The flask was rotated at a slow speed so as to tumble the solid Pergopak® M. About half of the NBPT solution was vacuum transferred onto the Pergopak® M over a 25-minute period at room temperature. The vacuum was then increased to 28 inches and the flask lowered into a warm water bath at 30-35° C. The remaining NBPT solution was slowly added over a 75-minute period. After an additional 14 minutes of mixing the flask was removed from the Rotavapor® and transferred into an open pan and allowed to air dry in a fume hood overnight. The final weight of the Pergopak® M loaded with the NBPT solution was 66.2 grams of a fine white free flowing powder.

Example 8

Pergopak® M Loading Using a 45.8 wt. % Solution of NBPT (N-n-butylthiophosphoric triamide) in THF (tetrahydrofuran)

Into a 1 liter round bottom flask containing 4 internal baffles was weighed 25.8 grams of Pergopak® M. Into a 250 ml beaker was weighed 126.2 grams of the 45.8 wt. % solution of NBPT in THF. The following loading procedure was used: (1) Approximately 25 grams of the NBPT solution was added to the Pergopak® M using a plastic pipette. (2) The flask was attached to a solvent evaporator (Buchi Rotavapor®) and rotated for 30-60 minutes at a slow speed so as to tumble the solid Pergopak® M. (3) The flask was then put under full vacuum and lowered into a warm water bath at 45 C for 15-50 minutes. The flask was then removed from the Rotavapor® and steps (1) through (3) were repeated until all of the NBPT solution had been loaded. The final weight of the Pergopak® M loaded with the NBPT solution was 86.2 grams of a fine white powder containing some agglomerates.

Example 9

Storage Stability of Pergopak® M Loaded with NBPT in the Presence and Absence of NMP Pergopak® M loaded with NBPT from examples 1 through 6 were stored in closed glass jars at room temperature for 8 months. During this study it was observed that the samples of Pergopak® M loaded with NBPT in the presence of NMP (Examples 1, 2 & 3) became clumpy and discolored over time while the samples of Pergopak® M loaded without the use of NMP (Examples 4, 5 & 6) remained white and free flowing. The NBPT content of the samples was by HPLC analysis over time. The results are given in the table below:

| Sample No. | Assay at time zero | Assay after 4 months | Assay after 8 months | % Loss after 8 months |
|---|---|---|---|---|
| Example 1 | 31.6 wt. % | 26.7 wt. % | 23.2 wt. % | 26.6% |
| Example 2 | 28.5 wt. % | 23.3 wt. % | 19.4 wt. % | 31.9% |
| Example 3 | 30.8 wt. % | 26.2 wt. % | 21.1 wt. % | 31.5% |
| Example 4 | 61.0 wt. % | 57.0 wt. % | 54.2 wt. % | 11.1% |
| Example 5 | 64.2 wt. % | 58.3 wt. % | 53.7 wt. % | 16.4% |
| Example 6 | 65.0 wt. % | 59.7 wt. % | 56.6 wt. % | 12.9% |

As the data shows the samples of this invention (Examples 4, 5 & 6) not only had a loading level over twice the level of Examples 1 through 3 but also had superior shelf life.

The invention claimed is:

1. A urea-formaldehyde polymer coated with one or more active ingredients wherein one active ingredient is a urease inhibitor, and wherein the concentration of the urease inhibitor is greater than about 35 wt. %, based on the total weight of the coated urea-formaldehyde polymer.

2. The urea-formaldehyde polymer of claim 1, said urea-formaldehyde polymer made by
   a) a process comprising depositing said active ingredient onto the urea-formaldehyde polymer, wherein said active ingredient is deposited onto said urea-formaldehyde polymer by contacting, in a drying device, a urea-formaldehyde polymer with a solution comprising a solvent selected from the group consisting of ethers, alcohols, hydrocarbons, halogenated hydrocarbons and aromatic hydrocarbons and said active ingredient under conditions including elevated temperatures and sub-atmospheric pressures thereby forming a coated urea-formaldehyde polymer; or
   b) a process comprising contacting a urea-formaldehyde polymer with a solution comprising tetrahydrofuran and said active ingredient under conditions including elevated temperatures and sub-atmospheric pressures thereby forming a coated urea-formaldehyde polymer.

3. The urea-formaldehyde polymer according to claim 1 wherein said urease inhibitor is NBPT.

4. The urea-formaldehyde polymer according to claim 1 wherein the active ingredient concentration is in the range of from about 40 wt. % to about 80 wt. %, based on the total weight of the coated urea-formaldehyde polymer.

5. The urea-formaldehyde polymer according to claim 1 wherein the active ingredient concentration is in the range of from about 50 wt. % to about 80 wt. %, based on the total weight of the active-ingredient-coated urea-formaldehyde polymer.

6. The urea-formaldehyde polymer according to claim 1 wherein the active ingredient concentration is in the range of from about 50 wt. % to about 70 wt. %, based on the total weight of the active-ingredient-coated urea-formaldehyde polymer.

7. A method comprising using the urea-formaldehyde polymer according to claim 1 in agricultural applications.

8. The urea-formaldehyde polymer according to claim 1 wherein the active ingredient concentration is in the range of from about 60 to about 70 wt. % based on the total weight of the active-ingredient-coated urea-formaldehyde polymer.

9. The urea-formaldehyde polymer according to claim 1 wherein the active ingredient concentration is in the range of from about 61 to about 65 wt. % based on the total weight of the active-ingredient-coated urea-formaldehyde polymer.

10. The urea-formaldehyde polymer according to claim 1 wherein the active ingredient concentration is about 70 wt. % based on the total weight of the active-ingredient-coated urea-formaldehyde polymer.

11. The urea-formaldehyde polymer according to claim 1 wherein said urea-formaldehyde polymer is selected from those having a water content of between from about 1 and 80 wt. %, based on the weight of the urea-formaldehyde polymer.

12. The urea-formaldehyde polymer according to claim 1 wherein said urea-formaldehyde polymer is selected from those having a water content of between from about 10 and 35 wt. %, based on the weight of the urea-formaldehyde polymer.

13. The urea-formaldehyde polymer according to claim 2 wherein said drying device is selected from the group consisting of a high shear mixer, a ribbon drier, a blade drier, and other similar devices.

14. The urea-formaldehyde polymer according to claim 13 wherein said drying device is selected from a ribbon drier and a blade drier.

15. The urea-formaldehyde polymer according to claim 14 made by a process wherein said urea-formaldehyde polymer and solution are introduced into the drying device i) simultaneously, ii) in stages, iii) either the polymer or solution introduced before the other, iv) or any combinations thereof.

16. The urea-formaldehyde polymer according to claim 15 wherein said process is either batch or continuous.

17. The urea-formaldehyde polymer according to claim 15 wherein the solution is introduced into the drying device after the urea-formaldehyde polymer.

18. The urea-formaldehyde polymer according to claim 15 wherein the introduction of the solution is at a rate substantially equal to the rate at which the solvent volatilizes.

19. The urea-formaldehyde polymer according to claim 2 wherein said elevated temperatures are in the range of from about 20° C. to about 200° C. and said sub-atmospheric pressures are in the range of from about 760 mmHg to about 0.1 mmHg.

20. The urea-formaldehyde polymer according to claim 19, wherein said elevated temperatures are in the range of from about 20° C. to about 100° C. and said sub-atmospheric pressures are in the range of from about 500 mmHg to about 50 mmHg.

21. The urea-formaldehyde polymer according to claim 20, wherein said elevated temperatures are in the range of from about 20° C. to about 50° C. and said sub-atmospheric pressures are in the range of from about 100 mmHg to about 50 mmHg.

* * * * *